United States Patent
Luo et al.

(10) Patent No.: US 10,472,349 B2
(45) Date of Patent: Nov. 12, 2019

(54) SALT OF PYRIDINYL AMINO PYRIMIDINE DERIVATIVE, PREPARATION METHOD THEREFOR, AND APPLICATION THEREOF

(71) Applicant: SHANGHAI ALLIST PHARMACEUTICALS, INC., Shanghai (CN)

(72) Inventors: Huibing Luo, Shanghai (CN); Huayong Zhou, Shanghai (CN)

(73) Assignee: SHANGHAI ALLIST PHARMACEUTICAL AND MEDICAL TECH CO, Shanghai (CN)

( * ) Notice: Subject to any disclaimer, the term of this patent is extended or adjusted under 35 U.S.C. 154(b) by 0 days.

(21) Appl. No.: 16/083,209

(22) PCT Filed: Mar. 1, 2017

(86) PCT No.: PCT/CN2017/000202
§ 371 (c)(1),
(2) Date: Sep. 7, 2018

(87) PCT Pub. No.: WO2017/152706
PCT Pub. Date: Sep. 14, 2017

(65) Prior Publication Data
US 2019/0100509 A1  Apr. 4, 2019

(30) Foreign Application Priority Data
Mar. 7, 2016  (CN) .......................... 2016 1 0126987

(51) Int. Cl.
*C07D 401/14* (2006.01)
*A61P 35/00* (2006.01)
*A61K 31/506* (2006.01)

(52) U.S. Cl.
CPC .......... *C07D 401/14* (2013.01); *A61K 31/506* (2013.01); *A61P 35/00* (2018.01)

(58) Field of Classification Search
CPC ...... C07D 401/14; A61P 35/00; A61K 31/506
See application file for complete search history.

(56) References Cited

U.S. PATENT DOCUMENTS

| 8,946,235 B2 | 2/2015 | Butterworth et al. |
| 2017/0210739 A1 | 7/2017 | Luo et al. |

FOREIGN PATENT DOCUMENTS

| CN | 103702990 A | 4/2014 |
| CN | 104761544 A | 7/2015 |
| CN | 105315259 A | 2/2016 |
| EP | 3181560 A1 | 6/2017 |
| WO | WO2016/015453 A1 | 2/2016 |
| WO | WO2017/152707 A1 | 9/2017 |

OTHER PUBLICATIONS

Berge et al., 66(1) J. Pharma. Sci. 1-19 (1977) (Year: 1977).*
International Search Report in Chinese with English translation, corresponding to International application No. PCT/CN2017/000202, dated Jun. 7, 2017, 6 pages.
Written Opinion in Chinese with English translation, corresponding to International application No. PCT/CN2017/000202, dated Jun. 7, 2017, 6 pages.
Supplemental European Search Report for European Application EP 17762392, dated Jun. 27, 2019, 5 pages.
Office Action from Japanese Patent Office in related Japanese Patent Application No. 2018-547437, dated Jul. 23, 2019, 3 pages. Machine translation included.

* cited by examiner

*Primary Examiner* — Timothy R Rozof
(74) *Attorney, Agent, or Firm* — Reising Ethington P.C.

(57) ABSTRACT

A mesylate salt of the compound of formula (I), the preparation method thereof, a pharmaceutical composition containing said salt and the use of said salt in treating diseases mediated by activating and resistance mutations of EGFR, in particular cancers, in mammal, in particular human. The mesylate salt of the compound of formula (I) has a high bioavailability in animal, and can remarkably inhibit the growth of transplanted tumors in animal and show a good safety.

(I)

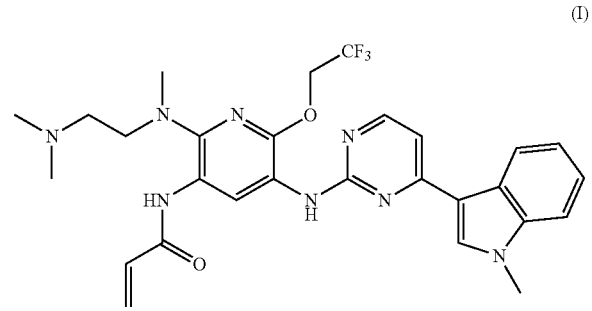

6 Claims, 1 Drawing Sheet

SALT OF PYRIDINYL AMINO PYRIMIDINE DERIVATIVE, PREPARATION METHOD THEREFOR, AND APPLICATION THEREOF

TECHNICAL FIELD

The present invention relates to a salt of pyridinylaminopyrimidine derivative. In particular, the present invention relates to the mesylate salt of N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide, the preparation method thereof, a pharmaceutical composition containing said salt, and the use of said salt in treating diseases mediated by activating and resistance mutations of EGFR, in particular cancers, in mammal, in particular human.

BACKGROUND

Epidermal cell growth factors receptors (EGFR) are identified as one significant driving factor in the process for cellular growth and proliferation. The epidermal cell growth factors receptors family is composed of EGFR (Erb-B1), Erb-B2 (HER-2/neu), Erb-B3 and Erb-B4. The epidermal cell growth factor receptors are associated with the process for most cancers, such as lung cancer, colon cancer, breast cancer and the like. The overexpression and mutation of EGFR have been proved to be the leading risk factor for a breast cancer with poor prognosis.

The current edge-cutting research is focused on an irreversible third-generation EGFR inhibitor. The patent application CN201410365911.4 discloses the following compound of formula (I), which compound has a substantially higher inhibition activity to the EGFR activating mutation (such as exon 19 deletion activating mutation, or L858R activating mutation) and T790M resistance mutation than the inhibition activity to the wild-type EGFR (WT EGFR), with a good selectivity, a relatively low toxicity side-effect and a good safety.

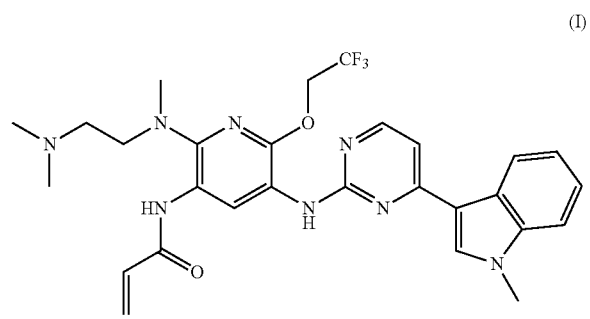 [SMILES: C=CC(=O)Nc1cc(Nc2nccc(-c3cn(C)c4ccccc34)n2)c(OCC(F)(F)F)nc1N(C)CCN(C)C]

(I)

SUMMARY OF THE INVENTION

A technical problem to be solved by the present invention is to provide the mesylate salt of the compound of formula (I), the preparation method thereof, a pharmaceutical composition containing said salt, and the use of said salt in treating diseases mediated by activating and resistance mutations of EGFR, in particular cancers, in mammal, in particular human.

In one aspect of the present invention there is provided a mesylate salt of the compound of formula (I).

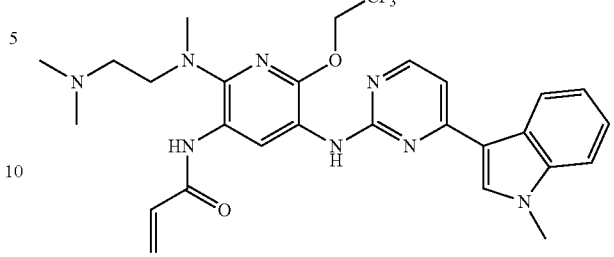

(I)

In some embodiments, the present invention provides the preparation method of the mesylate salt of the compound of formula (I).

In some embodiments, the present invention further provides a method for preparing the mesylate salt of the compound of formula (I), comprising directly reacting the compound of formula (I) with methanesulfonic acid in a solvent.

In some embodiments, the present invention provides a pharmaceutical composition, comprising the mesylate salt of the compound of formula (I) and a pharmaceutically acceptable carrier.

In some embodiments, the present invention further provides a pharmaceutical composition, comprising the mesylate salt of the compound of formula (I), and a pharmaceutically acceptable carrier, excipient or diluent.

In some embodiments, the present invention provides the mesylate salt of the compound of formula (I) for use as an anti-tumor medicament.

In some embodiments, the present invention also provides the use of the mesylate salt of the compound of formula (I) in manufacture of a medicament for treating diseases mediated by activating and resistance mutations of EGFR, in particular cancers in mammal, in particular human.

In some embodiments, the present invention also provides the use of the mesylate salt of the compound of formula (I) in manufacture of a medicament for treating cancers.

In some embodiments, the present invention also provides the use of the mesylate salt of the compound of formula (I) in treating diseases mediated by activating and resistance mutations of EGFR, in particular cancers in mammal, in particular human.

In some embodiments, the present invention also provides the use of the pharmaceutical composition containing the mesylate salt of the compound of formula (I) in manufacture of a medicament for treating diseases mediated by activating and resistance mutations of EGFR, in particular cancers in mammal, in particular human.

In some embodiments, the present invention also provides the use of the pharmaceutical composition containing the mesylate salt of the compound of formula (I) in manufacture of a medicament for treating cancer.

In some embodiments, the present invention also provides a method for treating diseases mediated by activating and resistance mutations of EGFR, in particular cancers in mammal, in particular human, including administering to a subject the mesylate salt of the compound of formula (I), or the pharmaceutical composition comprising a therapeutically effective amount of the mesylate salt of the compound of formula (I) and a pharmaceutically acceptable carrier, excipient or diluent.

In some embodiments, the present invention also provides a method of treating the cancer, including administering to a subject the mesylate salt of the compound of formula (I), or the pharmaceutical composition comprising a therapeutically effective amount of the mesylate salt of the compound of formula (I) and a pharmaceutically acceptable carrier, excipient or diluent.

The cancer as mentioned herein includes but is not limited to, for example, lung cancer, ovarian cancer, cervical cancer, breast cancer, stomach cancer, colorectal cancer, pancreatic cancer, glioma, glioblastoma, melanoma, prostate cancer, leukemia, lymphoma, non-Hodgkin's lymphoma, hepatocellular cancer, gastrointestinal stromal tumor (GIST), thyroid cancer, cholangiocarcinoma, endometrial cancer, renal cancer, anaplastic large cell lymphoma, acute myeloid leukemia (AML), multiple myeloma, and mesothelioma. In particular, the present invention in at least some embodiments has a good effect on the cancers having a mutation of the epidermal growth factor receptor, which mutation substitutes a threonine with a methionine at position 790 (EGFR T790M). For example, the mesylate salt of the compound of formula (I) can be used as a drug for treating the non-small cell lung cancer (EGFR T790M).

In another aspect of the present invention there is provided a method for preparing the compound of formula (I), which method refers to the method as disclosed in Example 1 of the patent application No. CN201410365911.4, wherein the preparation of Intermediate 1c and Intermediate 2a directly refers to the examples of the patent application No. CN201410365911.4.

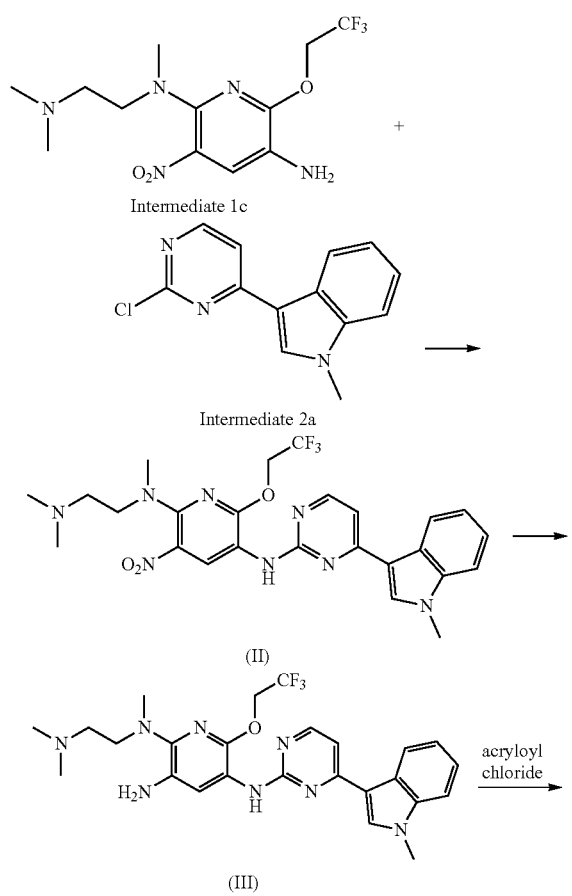

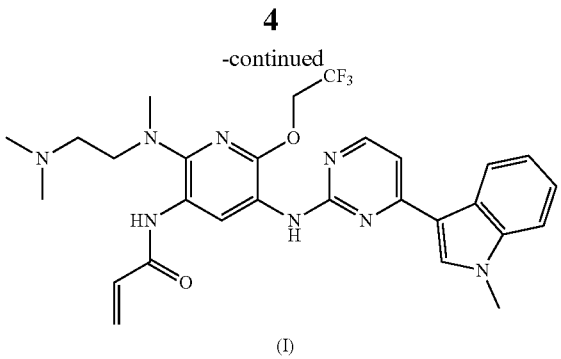

Intermediate 1c and Intermediate 2a are subjected to a substitution or coupling reaction to produce Compound (II). The nitro group of Compound (II) is reduced to produce Compound (III). Compound (III) and acryloyl chloride are subjected to acylation to produce Compound (I). The substitution or coupling reaction of Intermediate 1c and Intermediate 2a comprises those reactions that can be carried out under the catalysis by transition metal catalysts, wherein said transition metal catalysts include but are not limited to tris(dibenzylideneacetone)dipalladium/4,5-bis(diphenylphosphino)-9,9-dimethylxanthene. The reduction of the nitro group is carried out with the conventional reduction catalysts well known in the art, which include but are not limited to iron powder, zinc powder, sodium sulfide, $H_2$/platinum dioxide.

In some embodiments, the preparation method of the mesylate salt of the compound of formula (I) according to the present invention is as follows:

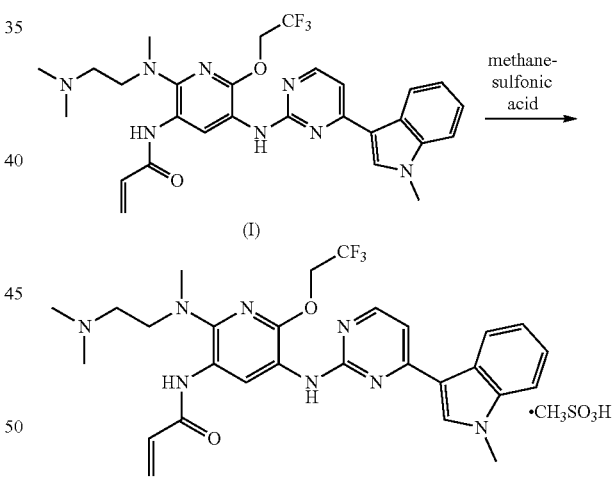

In a solvent, the compound of formula (I) and methanesulfonic acid may be directly reacted such that a salt is formed, to give the mesylate salt of the compound of formula (I). Said solvent may include but is not limited to a mixed solvent of acetone and water.

The mesylate salt of the compound of formula (I) may be administered to mammal including human, and can be administrated orally, rectally, parenterally (intravenously, intramuscularly or subcutaneously), topically (such as in the form of powders, ointments or drops), or intratumorally.

The mesylate salt of the compound of formula (I) may be administered at a dosage of about 0.05-50 mg/kg body weight/day, for example 0.1-45 mg/kg body weight/day, in a further example 0.5-35 mg/kg body weight/day.

The mesylate salts of the compound of formula (I) may be formulated into the solid dosage forms for oral administration, including but not limited to capsules, tablets, pills, powders, granules or the like. In these solid dosage forms, the mesylate salts of the compound of formula (I) as active ingredients may be admixed with at least one conventional inert excipients (or carriers), such as sodium citrate or dicalcium phosphate, or admixed with the following ingredients: (1) fillers or extenders, such as starch, lactose, sucrose, glucose, mannitol and silicic acid or the like; (2) binders, such as hydroxymethylcellulose, aginate, gelatin, polyvinylpyrrolidone, sucrose and arabic gum or the like; (3) humectants, such as, glycerol or the like; (4) disintegrating agents, such as agar, calcium carbonate, potato starch or tapioca starch, alginic acid, certain composite silicate, and sodium carbonate or the like; (5) retarding agents, such as paraffin wax or the like; (6) absorption enhancers, such as, quaternary ammonium compounds or the like; (7) moistening agents, such as cetanol and glyceryl monostearate or the like; (8) absorbents, such as, kaolin or the like; and (9) lubricants, such as, talc, calcium stearate, magnesium stearate, solid polyethylene glycol, sodium dodecyl sulphate or the like, or mixtures thereof. Capsules, tablets and pills may also comprise buffers.

Said solid dosage forms such as tablets, sugar pills, capsules, pills and granules can also be coated or microencapsulated by coatings and shell materials such as enteric coatings and other materials well known in the art. They may comprise opacifiers, and the release of active ingredients in these compositions may be carried out in a certain portion of digestive tract in a retarded manner. The examples for embedding components that may be adopted are polymer-based and wax-based substances. If necessary, active ingredients can also be formulated into the form of microcapsules with one or more of the above excipients.

The mesylate salts of the compound of formula (I) may be formulated into liquid dosage forms for oral administration, including but not limited to pharmaceutically acceptable emulsions, solutions, suspensions, syrups and tinctures or the like. Besides the mesylate salt of the compound of formula (I) as active ingredients, the liquid dosage forms may comprise inert diluents customarily used in the art, such as water and other solvents, solubilizers and emulsifiers, such as, ethanol, isopropanol, ethyl carbonate, ethyl acetate, propylene glycol, 1,3-butanediol, dimethyl formamide, and oils, especially cottonseed oil, peanut oil, corn germ oil, olive oil, castor oil and sesame oil and the like, or the mixtures thereof, and the like. Besides these inert diluents, the liquid dosage forms of the present invention may also comprise conventional adjuvants, such as moistening agents, emulsifiers and suspending agents, sweeting agents, flavoring agents and fragrances and the like.

Said suspending agents includes, such as, ethoxylated isostearyl alcohol, polyoxyethylene sorbitol and sorbitan ester, microcrystalline cellulose, aluminum methoxide and agar and the like, or the mixtures thereof.

The mesylate salts of the compound of formula (I) may be formulated into dosage forms for parenteral injection, including but not limited to physiologically acceptable sterile aqueous or non-aqueous solutions, dispersions, suspensions or emulsions, and sterile powder for re-dissolving into sterile injectable solutions or dispersions. Suitable carriers, diluents, solvents or excipients include water, ethanol, polyhydric alcohol and suitable mixtures thereof.

The compound of formula (I) or a pharmaceutically acceptable salt thereof can also be formulated into dosage forms for topical administration, including but not limited to ointments, powders, suppositories, drops, propellants and inhalants and the like. The mesylate salts of the compound of formula (I) as active ingredients are admixed together with physiologically acceptable carriers and optional preservatives, buffers, or if necessary, propellants, under sterile condition.

In some embodiments, the present invention also provides a pharmaceutical composition containing the mesylate salt of the compound of formula (I), and a pharmaceutically acceptable carrier, excipient or diluent. When preparing the pharmaceutical composition, the mesylate salt of the compound of formula (I) is generally admixed with the pharmaceutically acceptable carrier, excipient or diluent.

By conventional preparation methods, the composition may be formulated into conventional pharmaceutical preparations, such as tablets, pills, capsules, powders, granules, emulsions, suspensions, dispersions, solutions, syrups, elixirs, ointments, drops, suppositories, inhalants, propellants and the like.

The mesylate salt of the compound of formula (I) may be administered alone or in combination with other pharmaceutically acceptable therapeutic agents, especially with other anti-tumor drugs. The therapeutic agents include but are not limited to anti-tumor drugs which exert an effect on the chemical structure of DNA, such as cisplatin, anti-tumor drugs which affect the synthesis of nucleic acid, such as methotrexate (MTX), 5-fluorouracil (5FU) and the like, anti-tumor drugs which affect the transcription of nucleic acid, such as adriamycin, epirubicin, aclacinomycin, mitramycin and the like, anti-tumor drugs which exert an effect on synthesis of tubulin, such as paclitaxel, vinorelbine and the like, aromatase inhibitors such as aminoglutethimide, lentaron, letrozole, anastrozole and the like, inhibitors of the cell signal pathway such as epidermal growth factor receptor inhibitors imatinib, gefitinib, erlotinib, and the like. Each therapeutic agent to be combined can be administered simultaneously or sequentially, and can be administered either in a unitary formulation or in separate formulations. Such combination includes not only the combination of the compound of the present invention with another active ingredient, but also the combination of the compound of the present invention with two or more other active ingredients.

The determination method for the absolute bioavailability of the intragastric administration of the mesylate salts of the compound of formula (I) is as follows:

For intravenous administration: Healthy SD rats are randomly grouped. The tested compound is administered in a certain dosage D through the intravenous administration. The blood samples are collected through the retrobulbar venous plexus before the administration and 5 min, 15 min, 0.5 h, 1.0 h, 2.0 h, 4.0 h, 8.0 h, 12 h and 24 h after the administration, and separated to give plasmas. The concentration of the drug in plasma is determined with the liquid chromatography-tandem mass spectrometry method to give a drug concentration-time curve.

For intragastric administration: Healthy SD rats are randomly grouped. The tested substance is administered in a certain dosage D through the intragastric administration. The intravenous blood samples are collected through the rat's retrobulbar venous plexus before the administration and 0.5, 1.0, 2.0, 4.0, 6.0, 8.0, 10, 12 and 24 h after the administration, and separated to give plasmas. The concentration of the drug in plasma is determined with the liquid chromatography-tandem mass spectrometry method to give a drug concentration-time curve.

After dosage calibration, the absolute bioavailability F is calculated by the area under the drug concentration-time curve ($AUC_{0-t}$). The calculation equation is as follows:

$$F=(AUC_{intragastric} \times D_{intravenous})/(AUC_{intravenous} \cdot D_{intragastric}) \times 100\%.  \quad 5$$

The pharmacodynamics of the mesylate salts of the compound of formula (I) in terms of inhibiting the growth of transplanted tumors in animal may be assayed by conventional methods. One preferable evaluation method aims to the inhibitory effect on the growth of subcutaneously transplanted tumors of human lung cancer H1975-bearing nude mice. The experimental method may be as follows: human lung cancer H1975 cell strain ($5 \times 10^6$/each mouse) is inoculated to nude mice subcutaneously at the right side of the back thereof. After the tumors grow to 100-150 $mm^3$ on average, the animals are divided into groups randomly according to the tumor size and the animal weight. The test compounds are administered by intragastric administration in a certain dosages, and solvent control groups are administered with equal amount of solvent by intragastric administration, wherein the administration is performed once per day for a continuous period of 21 days. During the entire experimental process, the animal weight and the tumor size are measured twice per week, so as to observe whether or not the toxic reaction occurs.

The tumor volume is calculated as follows: Tumor volume ($mm^3$)=0.5×Tumor major diameter×Tumor minor diameter×Tumor minor diameter.

The beneficial technical effects produced by at least some embodiments of the present invention comprise:

The mesylate salt of the compound of formula (I) has an excellent bioavailability in animals.

The mesylate salt of the compound of formula (I) can remarkably inhibit the growth of transplanted tumors in animal and show a good safety.

Figure 1:
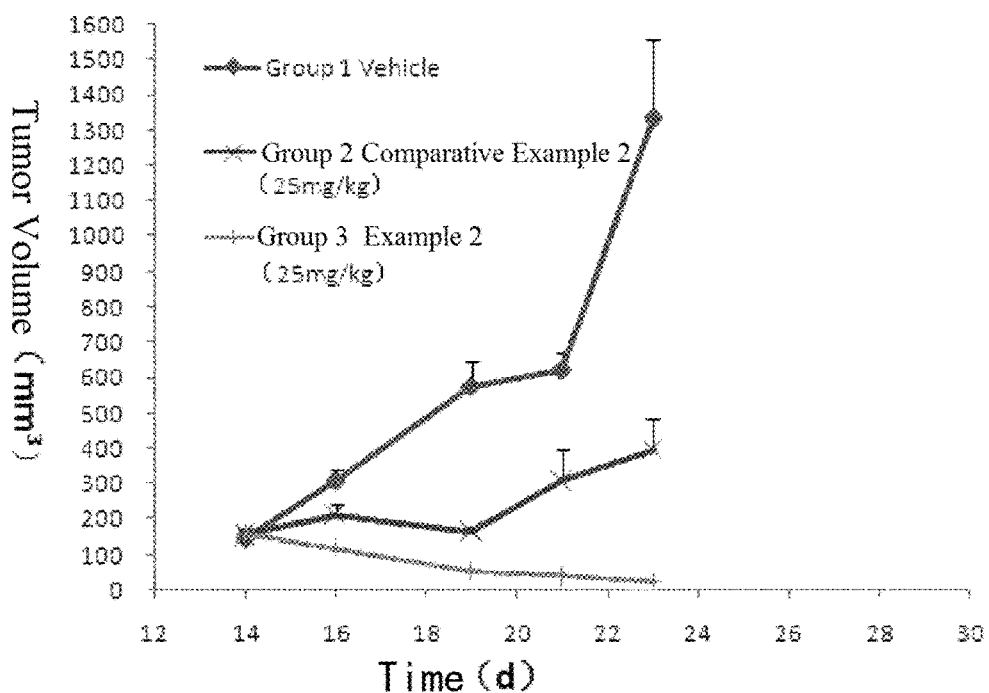
FIG. 1 is the tumor volume curve for subcutaneously transplanted tumors of human lung cancer H1975-bearing nude mice at the administration dosage of 25 mg/kg of the mesylate salt of the compound of formula (I) prepared according to Example 2 and the substance of Comparative Example 2 (i.e. Example 16 of patent application CN201410365911.4).

The present invention will be further illustrated hereinafter in connection with specific Examples. It should be understood that these Examples are only used to illustrate the present invention by the way of examples without limiting the scope thereof. In the following examples, the experimental methods without specifying conditions are generally performed according to conventional conditions or based on the conditions recommended by the manufacturer. The parts and percentages are the parts and percentages by weight respectively, unless otherwise specified.

DETAILED DESCRIPTION OF THE INVENTION

I. Preparation Example

Example 1

N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide Intermediate 1c:
$N^2$-methyl-$N^2$-[2-(dimethylamino)ethyl]-6-(2,2,2-trifluoroethoxy)-3-nitropyridine-2, 5-diamine, the preparation method thereof referring to the example disclosed in the patent application No. CN201410365911.4

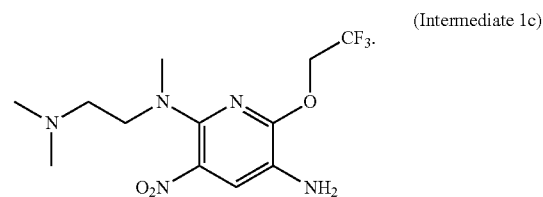 [SMILES: CN(C)CCN(C)c1nc(OCC(F)(F)F)c(N)cc1[N+](=O)[O-]]

(Intermediate 1c)

Intermediate 2a:
3-(2-chloropyrimidin-4-yl)-1-methyl-1H-indole, the preparation method thereof referring to the example disclosed in the patent application No. CN201410365911.4

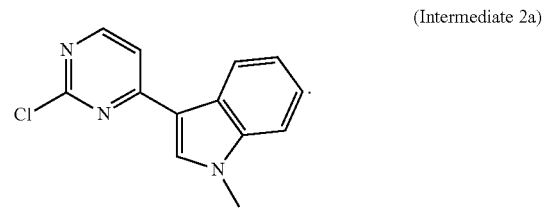 [SMILES: Cn1cc(-c2ccnc(Cl)n2)c2ccccc21]

(Intermediate 2a)

Compound (II)

Synthesis of $N^2$-methyl-$N^2$-[2-(dimethylamino)ethyl]-6-(2,2,2-trifluoroethoxy)-$N^5$-[4-(1-methyl-1H-indol-3-yl)pyrimidin-2-yl]-3-nitropyridine-2,5-diamine

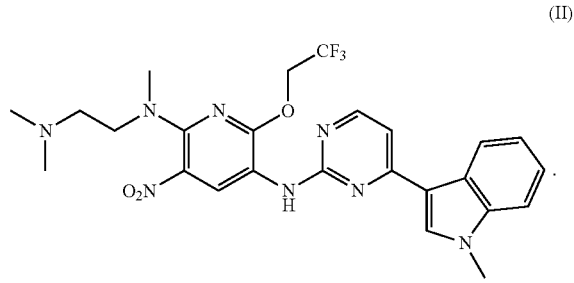

(II)

To a round bottom flask were added 3-(2-chloropyrimidin-4-yl)-1-methyl-1H-indole (73 mg, 0.3 mmol), $N^2$-methyl-$N^2$-[2-(dimethylamino)ethyl]-6-(2,2,2-trifluoroethoxy)-3-nitropyridine-2,5-diamine (100 mg, 0.3 mmol), tris(dibenzylideneacetone)dipalladium (14 mg, 0.015 mmol), 4,5-bis(diphenylphosphino)-9,9-dimethylxanthene (14 mg, 0.03 mmol), potassium phosphate (127 mg, 0.6 mmol) and 8 ml dioxane. The mixture was reacted under the protection of argon gas at 95° C. for 5 hours, and filtered. The filtrate was evaporated under vacuum to dryness, and purified by a silica gel column chromatography (dichloromethane:methanol=20:1) to give 140 mg of the product in a yield of 86%. MS m/z: 545 [M+1].

Compound (III)

Synthesis of $N^2$-methyl-$N^2$-[2-(dimethylamino)ethyl]-6-(2,2,2-trifluoroethoxy)-$N^5$-[4-(1-methyl-1H-indol-3-yl)pyrimidin-2-yl]pyridine-2,3,5-triamine

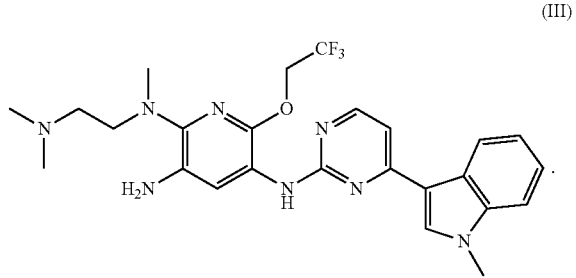 [SMILES: CN(C)CCN(C)c1nc(OCC(F)(F)F)c(Nc2nccc(-c3cn(C)c4ccccc34)n2)cc1[N+](=O)[O-]]

(III)

To a round bottom flask were added $N^2$-methyl-$N^2$-[2-(dimethylamino)ethyl]-6-(2,2,2-trifluoroethoxy)-$N^5$-[4-(1-methyl-1H-indol-3-yl)pyrimidin-2-yl]-3-nitropyridine-2,5-diamine (150 mg, 0.27 mmol), platinum dioxide (60 mg) and 10 ml of methanol. Then hydrogen was introduced. The mixture was reacted at room temperature for 1 h, filtered, and separated with a preparative plate (dichloromethane:methanol=10:1) to give 80 mg of the target compound in a yield of 56%. MS m/z: 515 [M+1].

Compound (I)

Synthesis of N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide

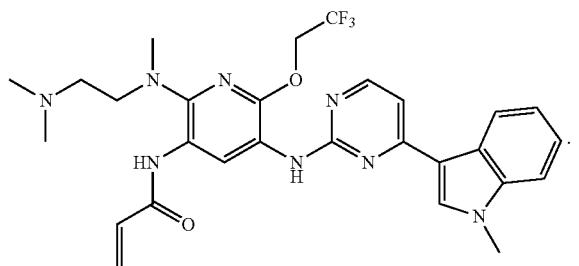

(I)

To a round bottom flask were added $N^2$-methyl-$N^2$[2-(dimethylamino)ethyl]-6-(2,2,2-trifluoroethoxy)-$N^5$-[4-(1-methyl-1H-indol-3-yl)pyrimidin-2-yl]pyridine-2,3,5-triamine (80 mg, 0.16 mmol) and 5 ml dichloromethane, and the mixture was cooled in an ice-water bath. 0.5 N of a solution of acryloyl chloride in dichloromethane (0.5 ml, 0.25 mmol) was added. The resulting mixture was reacted in an ice-water bath for 1.5 hours, and diluted with 50 ml ethyl acetate, and washed with a saturated sodium bicarbonate solution. The organic phase was dried with anhydrous sodium sulfate, and filtered. The filtrate was concentrated under vacuum, and purified by separating with a preparative plate (dichloromethane:methanol=10:1) to give 20 mg of the target product in a yield of 23%. MS m/z: 569 [M+1].

$^1$H NMR (400 MHz, DMSO-d6) δ 10.41 (s, 1H), 10.27 (s, 1H), 8.68 (s, 1H), 8.44 (s, 1H), 8.28 (t, J=8.5 Hz, 2H), 8.18 (s, 1H), 7.52 (d, J=8.0 hz, 1H), 7.29-7.14 (m, 3H), 6.98 (s, 1H), 6.28 (d, J=17.1 Hz, 1H), 5.76 (d, J=10.4 Hz, 1H), 5.00 (q, J=9.0 hz, 2H), 3.89 (s, 3H), 3.61 (s, 2H), 3.28 (s, 2H), 2.80 (s, 3H), 2.73 (s, 6H).

Example 2

Synthesis of the mesylate salt of N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide

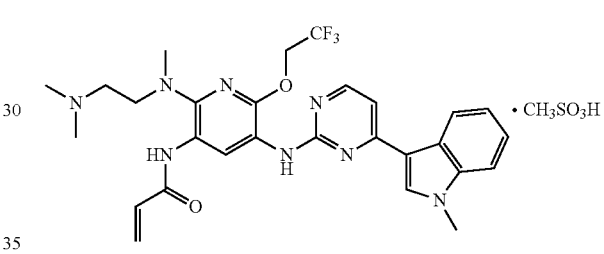

To a three-neck flask were added N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide (1 g, 1.76 mmol), acetone (35 ml), water (7 ml), and methanesulfonic acid (169 mg). The mixture was heated at 50° C. until dissolved, and evaporated under vacuum to dryness. Acetonitrile was added, and the resulting mixture was evaporated under vacuum to dryness. To the residue was added acetone. The resulting mixture was ultrasonically treated, and filtered. The filter cake was dried to give 685 mg of the target product in a yield of 59%.

$^1$H NMR (400 MHz, DMSO-d6) δ 9.80 (s, 1H), 9.23 (s, 1H), 8.53 (s, 1H), 8.42 (s, 1H), 8.30 (d, J=5.4 Hz, 2H), 8.23 (s, 1H), 7.52 (d, J=8.2 Hz, 1H), 7.25 (t, J=7.2 Hz, 1H), 7.22 (d, J=8.0 Hz, 1H), 7.15 (t, J=7.4 Hz, 1H), 6.70 (dd, J=17.0, 10.2 Hz, 1H), 6.34 (dd, J=17.0, 1.7 Hz, 1H), 5.83 (dd, J=10.3, 1.6 Hz, 1H), 5.02 (q, J=9.1 Hz, 2H), 3.88 (s, 3H), 3.65 (t, J=6.0 hz, 2H), 3.33 (t, J=6.0 hz, 2H), 2.86 (s, 6H), 2.81 (s, 3H), 2.44 (s, 3H).

II. Activity Test Examples

Test Example 1: Drug Absorption Experiments in SD Rats (Sprague Dawley Rats)

For intravenous administration: 16 healthy (half male and half female) SD rats with 200-280 g body weight, provided by Shanghai Sippr-BK laboratory animal Co. Ltd., were assigned randomly to 4 groups. The substances of the above Example 1, Example 2, Comparative Example 1 and Comparative Example 2 were intravenously administered in the dosage as shown in the following table. 0.2 ml of the intravenous blood samples were collected through the rat's retrobulbar venous plexus before the administration and 5 min, 15 min, 0.5 h, 1.0 h, 2.0 h, 4.0 h, 8.0 h, 12 h and 24 h after the administration, and separated to give plasmas. The concentration of the drug in plasma was determined with the liquid chromatography-tandem mass spectrometry method to give a drug concentration-time curve.

The main pharmacokinetic parameters are shown in Table 1 below:

TABLE 1

| Parameters | Example 1 | Example 2 | Comparative Example 1 | Comparative Example 2 |
|---|---|---|---|---|
| Dosage D(mg/kg) | 2.5 | 4.0 | 3.0 | 4.0 |
| $C_{max}$ (ng/mL) | 81.3 | 429.7 | 327.5 | 630.2 |
| $AUC_{0-t}$ (ng · h/mL) | 307.3 | 405.9 | 437.8 | 810.7 |
| $T_{1/2}$ (h) | 3.96 | 3.13 | 2.72 | 1.71 |

In Table 1, the substance structure of Comparative Example 1 is shown below and was prepared according to Example 2 of the patent application CN201410365911.4.

(Comparative Example 1)

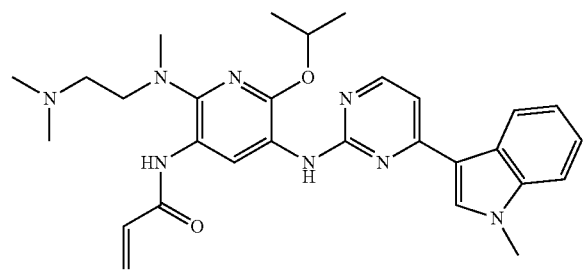

The substance structure of Comparative Example 2 is shown below and was prepared according to Example 16 of the patent application CN201410365911.4.

(Comparative Example 2)

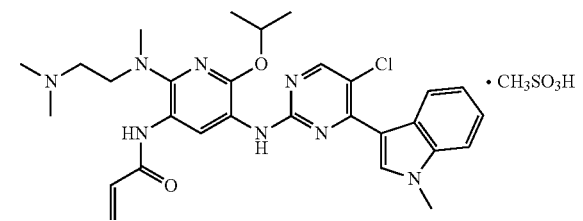

$T_{1/2}$: elimination half-life; $C_{max}$: maximum drug concentration in plasma; $AUC_{0-t}$: area under drug concentration-time curve.

For intragastric administration: 16 healthy (half male and half female) SD rats with 200-280 g body weight, provided by Shanghai Sippr-BK laboratory animal Co. Ltd., were assigned randomly to 4 groups. The substances of the above Example 1, Example 2, Comparative Example 1 and Comparative Example 2 were intragastrically administered in the dosage as shown in the following table. 0.2 ml of the intravenous blood samples were collected through the rat's retrobulbar venous plexus before the administration and 0.5, 1.0, 2.0, 4.0, 6.0, 8.0, 10, 12 and 24 h after the administration, and separated to give plasmas. The concentration of the drug in plasma was determined with the liquid chromatography-tandem mass spectrometry method to give a drug concentration-time curve.

Its main pharmacokinetic parameters are shown in Table 2:

| Parameters | Example 1 | Example 2 | Comparative Example 1 | Comparative Example 2 |
|---|---|---|---|---|
| Dosage D (mg/kg) | 10 | 10 | 6 | 10 |
| $C_{max}$ (ng/mL) | 17.6 | 44.54 | 12.63 | 28.3 |
| $AUC_{0-t}$ (ng · h/mL) | 231.7 | 287 | 77.66 | 172.2 |
| $T_{1/2}$ (h) | 4.14 | 8.33 | 8.60 | 5.76 |
| F (%) | 18.85 | 28.28 | 8.9 | 8.5 |

In table 2, the structures and the preparation methods of Comparative Examples 1 and 2 are identical to those in Table 1.

After dosage calibration, the absolute bioavailability F was obtained by calculation of $AUC_{0-t}$. The calculation equation was as follows:

$$F = (AUC_{intragastric} \times D_{intravenous}) / (AUC_{intravenous} \times D_{intragastric}) \times 100\%.$$

The obtained absolute bioavailability F data are shown in the above table 2.

Conclusion: the absolute bioavailability for intragastric administration of the mesylate salt of the compound of formula (I) of Example 2 was up to 28.28%, and remarkably better than the absolute bioavailability for intragastric administration of the compound of formula (I) according to Example 1, Comparative Example 1 and Comparative Example 2.

Test Example 2: Inhibition Effect on the Growth of Subcutaneously Transplanted Tumors of Human Lung Cancer H1975-Bearing Nude Mice The Inhibition effects of the mesylate salt of the compound of formula (I) prepared according to Example 2 and the substance of Comparative Example 2 (the structure of Comparative Example 2 is shown below and was prepared with reference to Example 16 of patent application CN201410365911.4) on subcutaneously transplanted tumors of human lung cancer H1975-bearing nude mice were observed.

(Comparative Example 2)

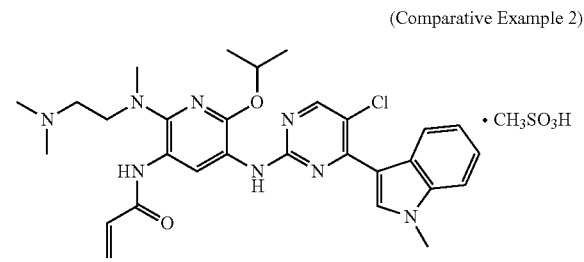 [SMILES: C=CC(=O)Nc1cc(Nc2ncc(Cl)c(-c3cn(C)c4ccccc34)n2)c(OC(C)C)nc1N(C)CCN(C)C ; "CH3SO3H"]

Cell cultivation: H1975 was placed in a RPMI-1640 medium containing 10% FBS, and cultivated in a temperature-constant incubator containing 5% $CO_2$ at 37° C. The cells in exponential growth phase were collected and counted for inoculation.

Test animals: 15 male BALB/c nude mice, 6 weeks old, 18-20 g, 5 mice in each group, commercially available from Shanghai Experiment Animal Research Center.

Three test groups were established: the control group of 0.5% sodium carboxymethylcellucose solvent, the group of Example 2 (25 mg/kg) and the group of Comparative Example 2 (25 mg/kg).

Experimental method: human lung cancer H1975 cell strain ($5\times10^6$/each mouse) was inoculated to nude mice subcutaneously at the right side of the back thereof. The tumor growth was observed regularly. The diameter of transplanted tumor was measured with vernier caliper. After the tumors grew to 100-150 mm$^3$ on average, the mice were divided into groups randomly according to the tumor size and the mouse weight. The substances of Example 2 and Comparative Example 2 were administered by intragastric administration in the dosage of 25 mg/kg, and the solvent control group was administered with equal amount of solvent by intragastric administration, wherein the administration was performed once per day for a continuous period of 21 days. During the entire experimental process, the mouse weight and the tumor size were measured twice per week, so as to observe whether or not the toxic reaction occurs.

The tumor volume was calculated as follows: Tumor volume (mm$^3$)=0.5×Tumor major diameter×Tumor minor diameter×Tumor minor diameter.

Figure 2:
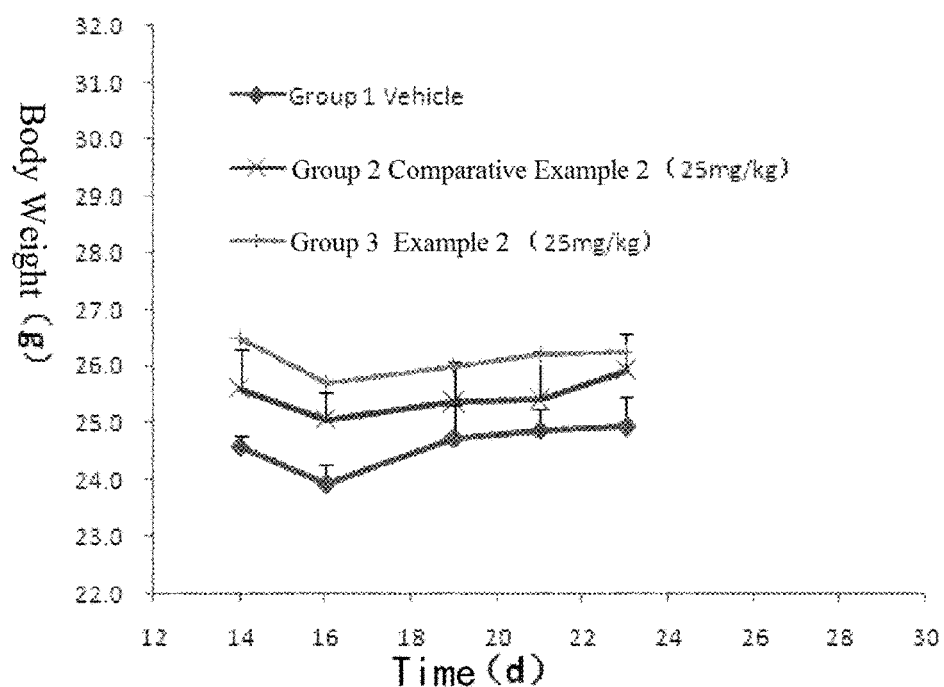
FIG. 2 is the body weight curve for human lung cancer H1975-bearing nude mice at the administration dosage of 25 mg/kg of the mesylate salt of the compound of formula (I) prepared according to Example 2 and the substance of Comparative Example 2 (i.e. Example 16 of patent application CN201410365911.4).

The tumor growth curve of three experimental groups was shown in FIG. 1, and the body weight curve was shown in FIG. 2.

Conclusion: the mesylate salt of the compound of formula (I) according to Example 2 had good inhibition effect on the growth of subcutaneously transplanted tumors of human lung cancer H1975-bearing nude mice, which was remarkably better than Comparative Example 2, and showed a good safety.

All of the literatures mentioned herein are hereby incorporated by reference. It should be also noted that, upon reading the above mentioned contents of the present application, a person skilled in the art can modify, change or amend the present invention without departing from the spirits and scope of the present invention, and these equivalents are also within the scope as defined by the claims appended in the present application.

The invention claimed is:

1. A mesylate salt of the compound of formula (I),

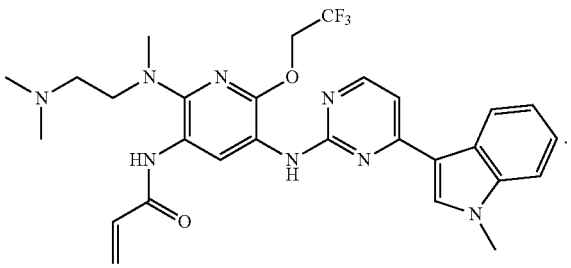

(I)

2. A method for preparing the mesylate salt of the compound of formula (I) according to claim 1, wherein, in a solvent, the compound of formula (I) and methanesulfonic acid are directly reacted to give the mesylate salt.

3. The method according to claim 2, wherein said solvent is a mixed solvent of acetone and water.

4. A pharmaceutical composition comprising: the mesylate salt of the compound of formula (I) according to claim 1; and a pharmaceutically acceptable carrier.

5. A method of treating a patient suffering from cancers, the method comprising administering to the patient the mesylate salt of the compound of formula (I) according to claim 1.

6. A method of treating a patient suffering from cancers, the method comprising administering to the patient the pharmaceutical composition according to claim 4.

* * * * *